(12) United States Patent
Hart et al.

(10) Patent No.: US 8,475,384 B2
(45) Date of Patent: Jul. 2, 2013

(54) THREE DIMENSIONAL IMAGING ULTRASOUND PROBE

(75) Inventors: Jeffrey Hart, Port Royal, PA (US);
Brian Moist, McVeytown, PA (US);
Dennis Clark, Lewistown, PA (US);
Daniel Agius, Newtown, CT (US)

(73) Assignee: Koninklijke Philips Electroncis N.V., Eindhoven (NL)

( * ) Notice: Subject to any disclaimer, the term of this patent is extended or adjusted under 35 U.S.C. 154(b) by 129 days.

(21) Appl. No.: 13/054,580

(22) PCT Filed: Jul. 22, 2009

(86) PCT No.: PCT/IB2009/053194
§ 371 (c)(1),
(2), (4) Date: Jan. 18, 2011

(87) PCT Pub. No.: WO2010/013175
PCT Pub. Date: Feb. 4, 2010

(65) Prior Publication Data
US 2011/0125025 A1      May 26, 2011

Related U.S. Application Data

(60) Provisional application No. 61/085,476, filed on Aug. 1, 2008.

(51) Int. Cl.
*A61B 8/14*      (2006.01)
(52) U.S. Cl.
USPC .......................................................... 600/459

(58) Field of Classification Search
USPC ..... 600/459, 437, 462; 310/317, 329; 73/633, 73/625, 636, 444
See application file for complete search history.

(56) References Cited

U.S. PATENT DOCUMENTS

| 4,437,468 | A |    | 3/1984  | Sorenson et al. |
|-----------|---|----|---------|---------------------------|
| 5,152,294 | A | *  | 10/1992 | Mochizuki et al. ........... 600/459 |
| 7,484,412 | B2| *  | 2/2009  | Hart et al. ....................... 73/618 |
| 7,635,335 | B2|    | 12/2009 | Hwang |
| 2003/0018269 | A1 |    | 1/2003  | Angelsen et al. |
| 2003/0229286 | A1 |    | 12/2003 | Lenker |
| 2005/0119576 | A1 | *  | 6/2005  | Li ................................... 600/459 |
| 2007/0016060 | A1 | *  | 1/2007  | Hwang ........................... 600/459 |

FOREIGN PATENT DOCUMENTS

| EP | 0133007 A    | 2/1985 |
| EP | 0707318 A    | 4/1996 |
| WO | 2005/096266 A | 10/2005 |

* cited by examiner

*Primary Examiner* — Long V. Le
*Assistant Examiner* — Lawrence Laryea

(57) ABSTRACT

An ultrasound probe includes a transducer array which is moved back and forth to sweep the image plane of the array through a volumetric region for 3D scanning. The transducer array is mounted on a carriage assembly which moves back and forth on a pair of rails inside a fluid compartment in the probe. The rails are preferentially arcuately curved to provide an elevationally divergent scan with a relatively wide aperture in the near field. A cam is provided for a motor-driven cable drive for the carriage assembly which provides relatively linear motion through the path of travel of the transducer array.

14 Claims, 6 Drawing Sheets

THREE DIMENSIONAL IMAGING ULTRASOUND PROBE

This invention relates to medical diagnostic ultrasound probes for imaging the body and, in particular, to ultrasound probes which perform three-dimensional (3D) scanning.

Common ultrasound imaging probes scan and provide echo information from a planar region of the body and the generation of a two-dimensional (2D) image. In recent years 3D probes have been developed for scanning and imaging volumetric regions of the body. Three-dimensional imaging probes enable an entire chamber of the heart to be viewed three dimensionally in real time, for example. The 3D probes for these application are in generally either electronic or mechanical. An electronic 3D probe steers the transmit beams in three dimensions electronically with a two-dimensional array transducer as illustrated in U.S. Pat. No. 5,997,479 (Savord et al.), for instance. With transducer elements extending in two dimensions, the transmit and receive beams can be steered in three dimensions by phased steering of the beams. A mechanical 3D probe uses a one-dimensional (1D) array transducer of the type used for standard 2D imaging and oscillates it back and forth. This causes the image plane of the 1D array to be swept through a volumetric region. The advantage of the mechanical 3D probe is that it uses conventional 1D array technology, but with the limitation that a mechanical arrangement to sweep the 1D array must be employed.

There are several ways to sweep the 1D array. One way is to spin the 1D array around its center as shown in U.S. Pat. No. 5,159,931 (Pini). The spinning of the 1D array will scan a cylindrical or conical volumetric region. Another approach is to rock the array back and forth so that the image plane will sweep through a wedge-shaped volumetric region. Examples of this sweeping technique are shown in U.S. Pat. Nos. 5,152,294 (Mochizuki et al.), 5,460,179 (Okunuki et al.) and 6,572,548 (Cerofolini). The wedge is narrow at the probe aperture and widens at deeper depths of the body. The mechanical probe of the '179 patent is particularly designed to have a sharp axis at the top of the wedge so that the probe can image from between the ribs.

These 3D mechanical scanning techniques all provide a volumetric image which is very narrow immediately in front of the probe. There are diagnostic applications, however, where it is desirable to have a wide field of view immediately in front of the probe. A wide field of view in the near field can be especially useful for fetal scanning, for example, where the fetus may be close to the wall of the abdomen. Accordingly it is desirable to have a mechanical 3D probe which scans a wide field of view immediately in front of the probe.

In accordance with the principles of the present invention, a 3D ultrasound probe is described which scans a wide field of view in front of the probe aperture. A 1D array transducer is mounted in the probe to travel back and forth over an integral rolling surface preferably formed as a curved set of rails in the probe. The transducer array is mounted on a carriage which is pulled back and forth over the rails by a belt or cable pulled by a motor. In an illustrated example of the present invention, the cable which moves the transducer carriage wraps around a cam which maintains proper tension on the cable as the carriage moves in its arcuate path of travel. In a constructed embodiment the motor oscillates the cam to pull the cable and move the 1D transducer array through its path of volumetric scanning.

IN THE DRAWINGS

Figure 1:
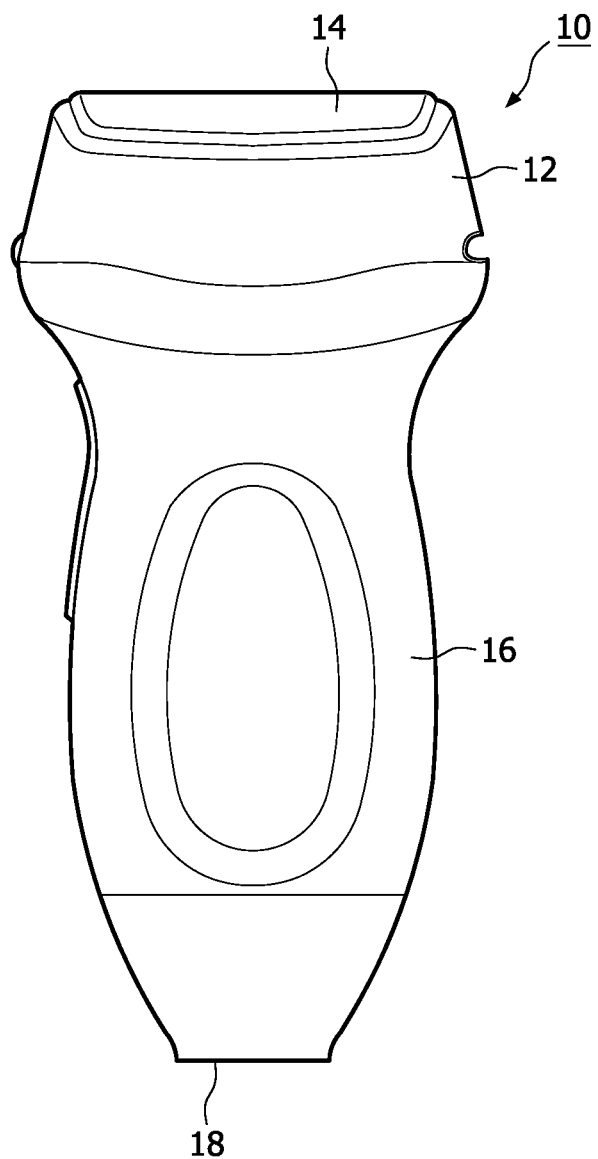
FIG. 1 illustrates an external view of a mechanical 3D probe of the present invention.

Referring first to FIG. 1, a 3D ultrasound probe 10 constructed in accordance with the principles of the present invention is shown in an external view. The probe includes an outer case having a distal end 12 in which a transducer assembly 20 (see FIG. 2) is mounted such that the image plane of a moving transducer array extends from a lens or end cap 14. The transducer array is located in a fluid compartment inside the distal end 12 containing fluid such as mineral oil which acoustically couples ultrasound energy between the transducer array and the end cap 14. As the transducer array moves back and forth its image plane is swept through a volumetric region in front of the end cap 14 to perform a 3D scan of the material in the volumetric region. In the distance between the transducer array and the exterior surface of the end cap 14 the image plane has diverged so that it can scan a relatively wide aperture in the near field just in front of the end cap. The probe 10 has a handle portion 16 below the distal end in which electrical connection is made to the terminating conductors of a cable from flex circuit conductors attached to the elements of the transducer array. The cable (not shown) extends from the probe case through a strain relief located at the proximal end 18 of the probe case. In use, a sonographer holds the probe by the handle portion and presses the end cap 14 against the skin of a patient to image the volumetric region of the patient's body in front of the end cap.

Figure 2:
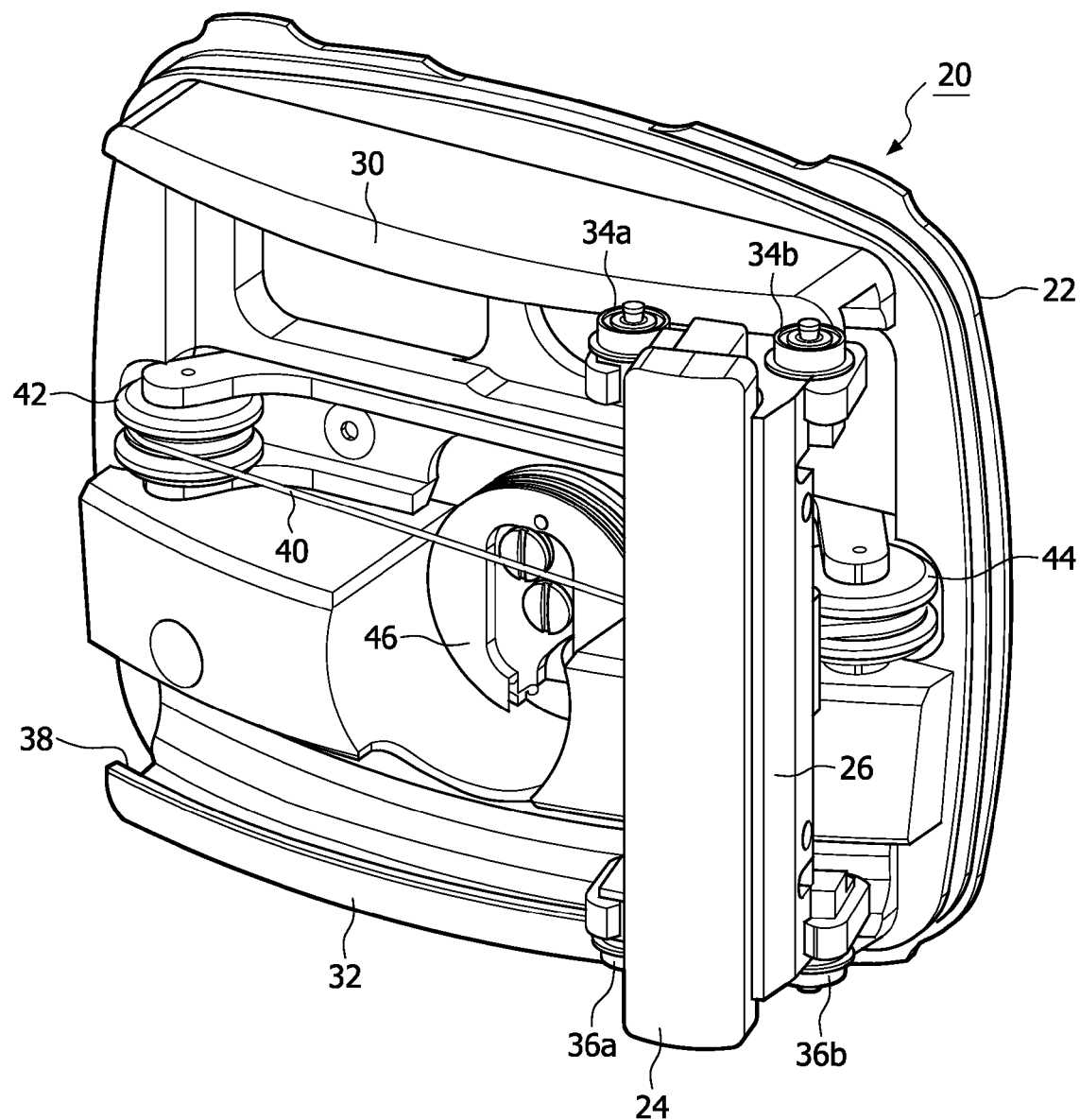
FIG. 2 is a perspective view of the mechanical assembly of a 3D probe of the present invention as viewed from above the transducer array.

FIG. 2 is a view of the transducer assembly 20 from above the transducer array 24. The transducer array 24 is mounted on a carriage assembly 26 which is pulled back and forth (from left to right and back again in FIG. 2) along a pair of rails 30,32. At each end of the carriage assembly is a set of ball bearing rollers 34,36 which ride on the rails 30,32. The carriage assembly 26 is pulled back and forth by a cable 40 attached to the underside of the carriage assembly as shown in greater detail in FIG. 5. From the points of attachment to the carriage assembly the cable 40 passes around a pair of idler pulleys 42,44 and then partially around circumferential grooves of a cam 46. The ends of the cable 40 are attached by screws in the middle of the cam 46. The cam is rotated back and forth by a brushless DC motor 80 attached to a cam shaft 48 extending from the bottom of the cam into the handle portion where the motor is located. See FIG. 3.

The aforementioned components of the transducer assembly 20 are mounted on a bulkhead 22. The bulkhead has grooves around its periphery which seat O-ring seals to seal the fluid compartment in which the carriage assembly 26 is located from the interior of the handle portion 16 of the probe in which the motor and transducer/cable electrical connections are located. The flex circuit from the transducer array 26 passes through a seal in the bulkhead to the interior of the handle portion and the cam shaft 48 of the cam is sealed by passage through a dynamic fluid seal in the bulkhead 22. A fluid passageway extends through the bulkhead for attachment to a non-elastomeric balloon in the handle portion which provides compensation for changes in fluid volume with pressure and temperature as described in international patent application publication WO2005/094690 (Wickline et al.)

The ball bearing rollers at the ends of the carriage assembly 26 are in sets of three rollers, two of which ride on the top of the rails 30,32 and one of which rides in an undercut 38 in the side of each rail. In the view of FIG. 2 rollers 34*a* and 34*b* at one end of the carriage assembly and rollers 36*a* and 36*b* at the other end of the carriage assembly are rollers which ride on the top surface of the rails 30 and 32. The rails 30,32 in this example are slightly curved in an arc. This slightly cylindrical profile of the rails defines the path of the carriage assembly motion and causes the plane of the transducer array to sweep through a trapezoidal volume rather than simply a square or rectangular volume, providing a wider field of view than would occur through the use of flat, linear rails. The successive image planes scanned by the array transducer as it travels back and forth thus diverge in the elevation direction of the planes as the transducer array is moved.

Figure 3:
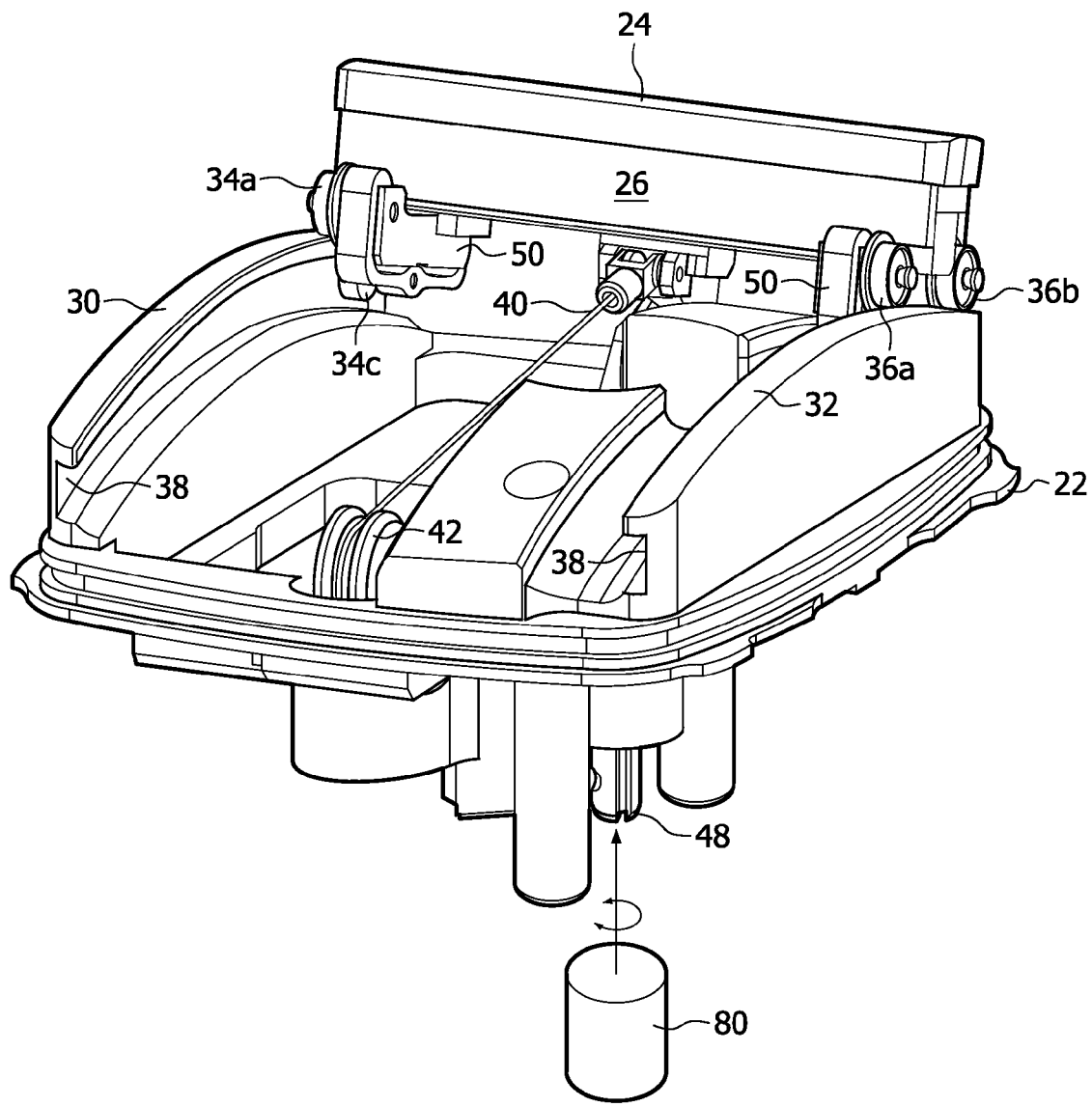
FIG. 3 is a perspective view of the mechanical assembly of FIG. 2 as viewed from the side.

FIG. 3 is a view of the transducer assembly 20 of FIG. 2 as seen from the side. In this view the rollers 36*a* and 36*b* can be seen riding on top of the rail 32 and roller 34*a* is seen riding on top of the rail 30. A roller 34*c* which rides in the undercut 38 of rail 30 is partially visible at the left side of the carriage assembly 26. The cylindrical arc of the rails 30,32 is also plainly shown in this drawing. The rollers are mounted to bearing mounts 50 which are attached to the bottom of the carriage assembly. The pivoting connection of the cable 40 to the underside of the carriage assembly is seen in this view. The cam shaft 48 is seen projecting from the bottom of the bulkhead 22.

Figure 4:
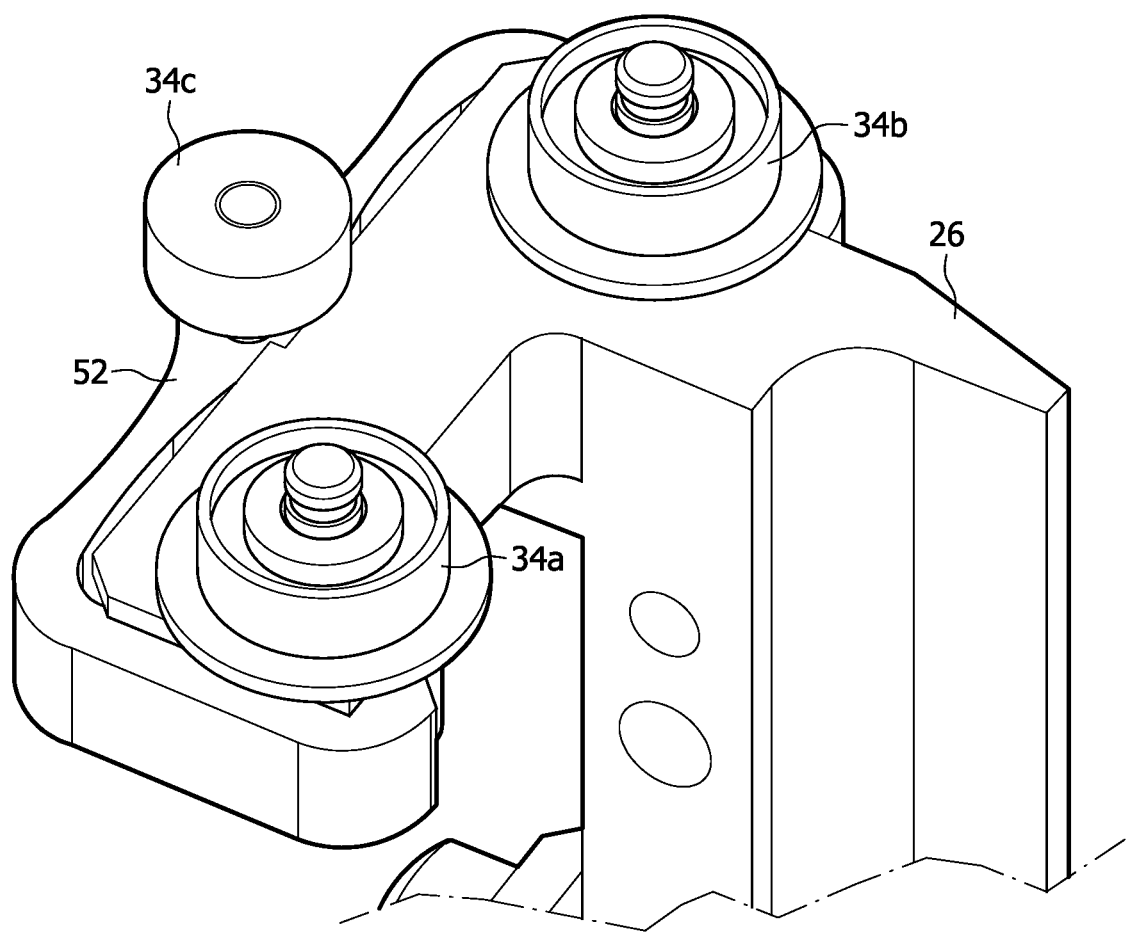
FIG. 4 is a detailed perspective view of the bearing structure at the end of the carriage of the mechanical assembly of FIG. 2.

FIG. 4 is another embodiment of the attachment of the rollers to the carriage assembly 26, in which the bearing mount 50 is integrally formed at the bottom of the carriage assembly 26. The upper rollers 34*a* and 34*b* are mounted to the side of the carriage assembly and a bearing clip 52 to which the lower bearing 34*c* which rides in the undercut 38 is attached provides preloading of the carriage assembly against the bulkhead 22.

Figure 5:
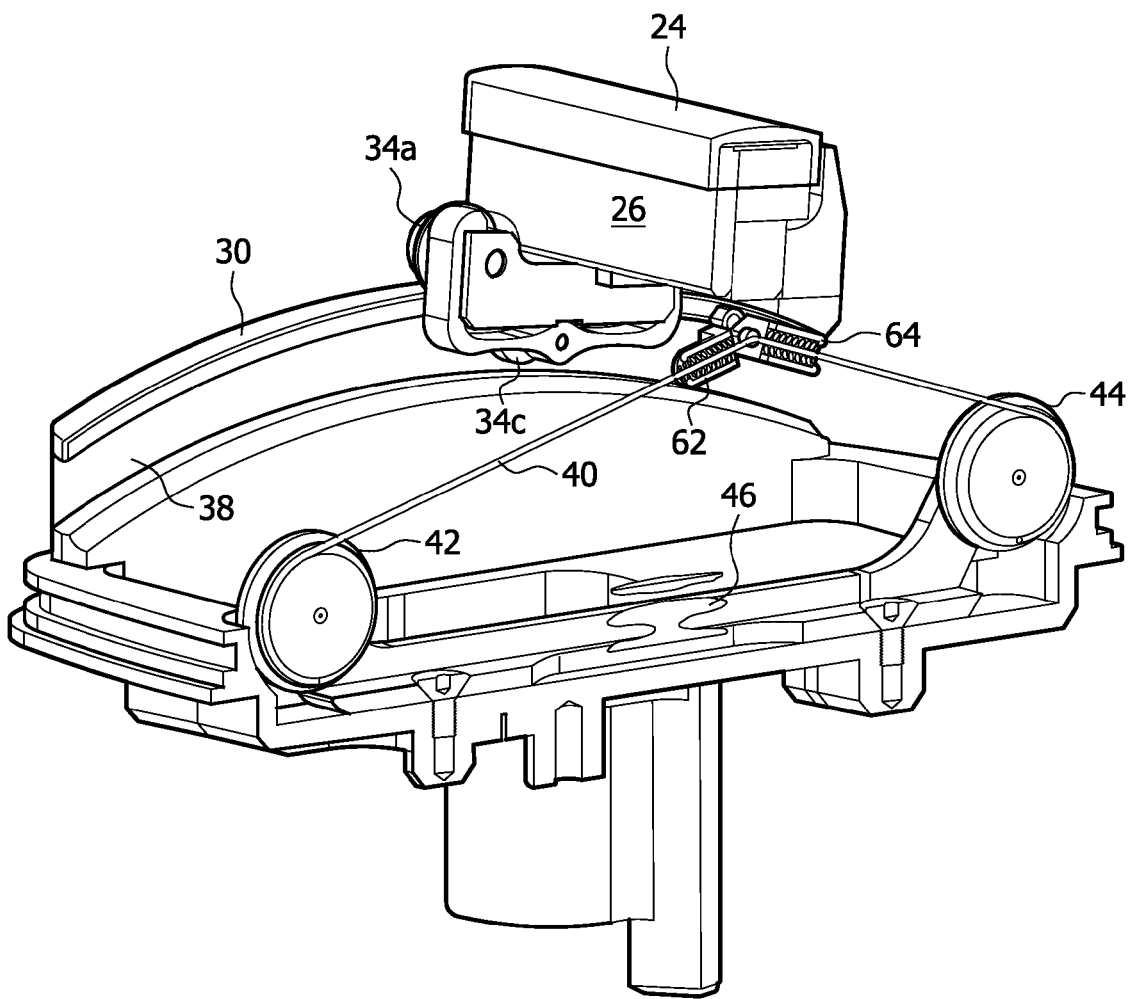
FIG. 5 is a cutaway perspective view illustrating the cable and idler pulleys of the mechanical assembly of FIG. 2.

FIG. 5 is a cutaway view through the centers of the idler pulleys 42 and 44. This view shows the connections of the ends of the cable to cable fittings 62,64 pivotally attached to the underside of the carriage assembly. Swage balls at the ends of the cable bear against springs inside the cable fittings which provide continuous tensioning of the cable as it pulls the carriage assembly 26 back and forth along the rails 30 and 32.

Figure 6:
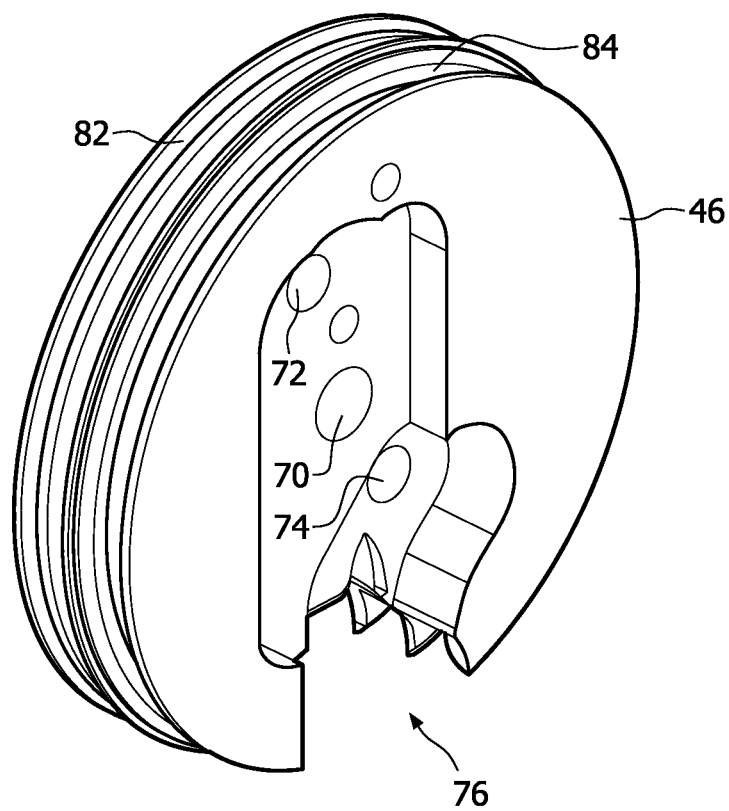
FIG. 6 is a perspective view of the drive cam of the mechanical assembly of FIG. 2.

FIG. 6 illustrates the cam 46 in a perspective view. The cable from the idler pulleys 42 and 44 wrap around the cam 46 in grooves 82 and 84 on the circumference of the cam, and the ends of the cable pass into the interior 76 of the cam and are attached to the cam by screws which are fastened in screw holes 72 and 74. A center screw hole 70 provides attachment of the cam axially to the cam shaft 48 on the back of the cam. In this example the cam is not perfectly circular but is slightly oblong. This eccentric shape of the cam causes the carriage assembly to travel with linear motion as it travels back and forth over the arcuate rails 30 and 32. The linear motion provides a uniform spacing of the ultrasound beams and image plane produced by the transducer array as it travels back and forth for a consistently scanned volumetric image. In a constructed embodiment the cam travels approximately 180° as it rotates first in one direction (e.g., clockwise) and then the other (counterclockwise) to move the carriage assembly from one end of the rails to the other and back again.

Other variations will readily occur to those skilled in the art. For instance, in lieu of a cable 40, ballscrews, belts, or a chain may be used to couple the motor to the carriage assembly. The rails do not have to be arcuately curved, but can be linear if a more rectangular volumetric scan is to be obtained. A cable driven rail mechanism as illustrated above can provide approximately a 40% reduction in weight as compared to the swing arm mechanisms of the prior art. This efficient, compact mechanism requires that only the motor for the mechanism be located in the handle, enabling the probe to be designed with a slimmer handle girth or grip size than is the case of other 3D mechanical probes of the prior art.

What is claimed is:

1. An ultrasonic probe which scans a volumetric region by movement of an array transducer comprising:

a probe case with an end cap having a fluid compartment at a distal end;

an array transducer mounted on a carriage assembly in the fluid compartment;

a pair of rails on which the carriage assembly travels in the fluid compartment;

a pair of rollers located at each end of the carriage assembly, two of the rollers riding on the top of the rails and two of the rollers riding on the bottom of the rails, the rollers rotating about axis of rotation directed across the pair of rails;

a drive cable connected to the carriage assembly;

a rotatable cam having a center axis about which the drive cable is wound; and a motor operatively coupled to move the carriage assembly and array transducer on the rails, wherein the rotatable cam is oriented so that the axis of rotation of the cam extends substantially orthogonal to the axis of rotation of the rollers.

2. The ultrasonic probe of claim 1, wherein the rollers are attached to the carriage assembly which rides on the rails.

3. The ultrasonic probe of claim 2, wherein the rollers further comprise a first ball bearing roller located at one side of the carriage assembly and riding on a first one of the rails, and a second ball bearing roller located at the other side of the carriage assembly and riding on a second one of the rails.

4. The ultrasonic probe of claim 3, wherein the rails further comprise an undercut region, and further comprising third and fourth rollers riding in the undercut region of each rail.

5. The ultrasonic probe of claim 1, wherein the motor is operatively coupled to move the carriage assembly by a cable coupled between the motor and the carriage assembly.

6. The ultrasonic probe of claim 5, wherein the cable passes around at least a portion of a cam surface to provide relatively linear motion to the carriage assembly.

7. The ultrasonic probe of claim 6, wherein the motor is coupled to the cam to drive the cam in alternating directions of rotation, wherein the ends of the cable are attached to the cam.

8. The ultrasonic probe of claim 6, wherein the cam surface of the cam is oblong to drive the carriage assembly in relatively linear motion between the ends of the rails.

9. The ultrasonic probe of claim 6, further comprising idler pulleys around which the cable passes between the carriage assembly and the cam.

10. The ultrasonic probe of claim 5, wherein the cable is coupled to the carriage assembly by a spring fitting for cable tensioning.

11. The ultrasonic probe of claim 1 wherein the probe case end cap comprises an end cap through which ultrasonic energy passes to and from the array transducer, wherein coupling fluid is located between the array transducer and the inner surface of the end cap.

12. The ultrasonic probe of claim 1, wherein the rails are curved to provide an arcuate path of travel for the array transducer.

13. The ultrasonic probe of claim 12, wherein the arcuate path of travel causes the image plane of the array transducer to diverge in the elevation direction as the array transducer is moved.

14. The ultrasonic probe of claim 1, wherein the rails are flat to provide a linear path of travel for the array transducer.

* * * * *